United States Patent
Ho et al.

(10) Patent No.: US 9,795,621 B2
(45) Date of Patent: Oct. 24, 2017

(54) METHODS AND MATERIALS FOR REDUCING ORGAN TRANSPLANT REJECTION OR ISCHEMIC/REPERFUSION INJURY IN A SUBJECT

(71) Applicant: Carnegie Mellon University, Pittsburgh, PA (US)

(72) Inventors: Chien Ho, Pittsburgh, PA (US); Li Liu, Pittsburgh, PA (US); Yijen Wu, Pittsburgh, PA (US); T. Kevin Hitchens, Pittsburgh, PA (US); Qing Ye, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 14/654,735

(22) PCT Filed: Sep. 6, 2013

(86) PCT No.: PCT/US2013/058598
§ 371 (c)(1),
(2) Date: Jun. 22, 2015

(87) PCT Pub. No.: WO2014/099056
PCT Pub. Date: Jun. 26, 2014

(65) Prior Publication Data
US 2015/0335664 A1 Nov. 26, 2015

Related U.S. Application Data

(60) Provisional application No. 61/848,127, filed on Dec. 20, 2012.

(51) Int. Cl.
*A61K 31/20* (2006.01)
*A61K 31/661* (2006.01)
*A61K 31/047* (2006.01)
*A61K 9/00* (2006.01)
*A61K 35/35* (2015.01)

(52) U.S. Cl.
CPC .......... *A61K 31/661* (2013.01); *A61K 9/0019* (2013.01); *A61K 31/047* (2013.01); *A61K 31/20* (2013.01); *A61K 35/35* (2013.01)

(58) Field of Classification Search
CPC .................................. A61K 31/20; A61K 8/04
See application file for complete search history.

(56) References Cited

U.S. PATENT DOCUMENTS

| | | | |
|---|---|---|---|
| 2008/0193374 A1 | 8/2008 | Larsen et al. | |
| 2011/0027348 A1* | 2/2011 | Feher | A61K 35/74 424/450 |
| 2011/0117192 A1 | 5/2011 | Navon et al. | |
| 2014/0274988 A1 | 9/2014 | Lippard et al. | |

FOREIGN PATENT DOCUMENTS

| | | |
|---|---|---|
| WO | WO2014/039874 | 3/2014 |
| WO | WO2014099056 | 6/2014 |
| WO | WO2016/134134 | 8/2016 |

OTHER PUBLICATIONS

Lutz et al. J. of Inflammation, 2010, vol. 7, No. 27, pp. 1-8.*
Siqueira et al. J. Clin. Endocr. Metab., 2011, vol. 96, No. 10, pp. 3207-3216.*
Arumugam, et al. "Toll-like receptors in ischemia-reperfusion injury," Shock, 32(1):4-16 (2009).
Bopassa JC, "Protection of the ischemic myocardium during the reperfusion: between hope and reality," Am. J. Cardiovas. Dis., 2(3):223-236 (2012).
Bulte and Kraitchman, "Iron oxide MR contrast agents for molecular and cellular imaging," NMR Biomed., 17(7):484-499 (2004).
Chan et al., "Ischaemia-reperfusion is an event triggered by immune complexes and complement" Br. J. Surg., 90(12):1470-1478 (2003).
Edwards et al., "Metabolomics reveals increased isoleukotoxin diol (12, 13-DHOME) in human plasma after acute Intralipid infusion," J. Lipid Res. 53(9):1979-1986 (2012).
Epelman and Mann, "Communication in the heart: the role of the innate immune system in coordinating cellular responses to ischemic injury," J. Cardiovas. Transl. Res., 5(6):827-3 (2012).
Harvery and Cave, "Intralipid infusion ameliorates propranolol-induced hypotension in rabbits," J. Med. Toxicol., 4(2):71-76 (2008).
Heidenreich, et al. "Forecasting the future of cardiovascular disease in the United States: a policy statement from the American Heart Association," Circulation 123(8):933-944 (2011).
Kinsey et al., "Regulatory T cells contribute to the protective effect of ischemic preconditioning in the kidney," Kidney International, 77(9):771-780 (2010).
Knight et al., "Cold ischemic injury, aortic allograft vasculopathy, and pro-inflammatory cytokine expression," J. Surg. Res. 113(2):201-207 (2003).
Kosieradzki and Rowinski, "Ischemia/reperfusion injury in kidney transplantation: mechanisms and prevention," Transplant Proc., 40(10):3279-3288 (2008).
Krogh-Madsen, et al. "Effect of short-term intralipid infusion on the immune response during low-dose endotoxemia in humans," Am J. Physiol. Endocrinol. Metab., 294(2):E371-379 (2008).
Lutz et al., "Anti-inflammatory treatment strategies for ischemia/reperfusion injury in transplantation," J. Inflamm. (Lond), 7:27 (2010).
Nahas et al., "Role of growth hormone in the development of experimental renal scarring," Kidney Int., 40(1):29-34 (1991).
Solez, K. et al., "The morphology of "acute tubular necrosis" in man: analysis of 57 renal biopsies and a comparison with the glycerol model," Medicine 58:362-376 (1979).
Stewart et al., "Revision of the 1990 working formulation for the standardization of nomenclature in the diagnosis of heart rejection," J. Heart Lung Transplant, 24(11):1710-1720 (2005).

(Continued)

*Primary Examiner* — Samira Jean-Louis
(74) *Attorney, Agent, or Firm* — Fish & Richardson P.C.

(57) ABSTRACT

Methods and materials for reducing organ transplant rejection or minimizing ischemia or ischemia/reperfusion injury in a subject are described. The methods include administering a fat emulsion before or after the organ transplant or before, at the onset of, or after the ischemic event.

16 Claims, 8 Drawing Sheets

(56) References Cited

OTHER PUBLICATIONS

Tanaka et al., "Prolonged cold ischemia in rat cardiac allografts promotes ischemia-reperfusion injury and the development of graft coronary artery disease in a linear fashion," J. Heart Lung Transplant, 24(11):1906-1914 (2005).
Van de Werf, et al., "Management of acute myocardial infarction in patients presenting with persistent ST-segment elevation: the Task Force on the Management of ST-Segment Elevation Acute Myocardial Infarction of the European Society of Cardiology," Eur. Heart J., 29(23):2909-2945 (2008).
Velasquez et al., "Perindopril ameliorates glomerular and renal tubulointerstitial injury in the SHR/N-corpulent rat," Hypertension, 30(5):1232-1237 (1997).
Vilaro and Llobera, "Uptake and metabolism of Intralipid by rat liver: an electron-microscopic study," J. Nutr. 118(8):932-940 (1988).
Wanten and Calder, "Immune modulation by parenteral lipid emulsions," Am. J. Clin. Nutr. 85(5):1171-1184 (2007).
Winter, et al., "The international society for heart and lung transplantation grading system for heart transplant biopsy specimens: Clarification and commentary," J. Heart Lung Transplant 17:754-760 (1998).
Wu et al., "MRI investigations of graft rejection following organ transplantation using rodent models," Method Enzymol. 386:73-105 (2004).
Ye et al., "In vivo detection of acute rat renal allograft rejection by MRI with USPIO particles," Kidney Int., 61(3):1124-1135 (2002).
Siamak Rahman et al., "Phosphorylation of GSK-3β mediates Intralipid-induced cardioprotection against Ischemia/Reperfusion injury," NIH Public Access Anesthesiology. Aug. 2011; 115(2):1-25.
Jingyuan Li et al., "Intralipid, a Clinically Safe Compound, Protects the Heart Against Ischemia-Reperfusion Injury More Efficiently Than Cyclosporine-A," NIH Public Access, Anesthesiology, Oct. 2012; 117(4):1-22.
Jarzyna et al., "Iron oxide core oil-in-water emulsions as a multifunctional nanoparticle platform for tumor targeting and imaging," 2009 Biomaterials 30:6947-6954.
Simberg et al., "Biomimetic amplification of nanoparticle homing to tumors," 2007 PNAS, 104:932-936.
Tobias Neuberger, et al., "Superparamagnetic nanoparticles for biomedical applications: Possibilities and limitations of a new drug delivery system," Journal of Magnetism and Magnetic Materials, 293:483-496 (2005).
C. Chouly et al., "Development of superparamagnetic nanoparticles for MRI: effect of particle size, charge and surface nature on biodistribution," J. Microencapsulation, 13(3):245-255 (1996).
E. Okon et al., "Biodegradation of Magnetite Dextran Nanoparticles in the Rat, A Histologic and Biophysical Study," Laboratory Investigation, 71(6):895-903 (1994).
Arvizo et al., "Modulating pharmacokinetics, tumor uptake and biodistribution by engineered nanoparticles," PLoS One, 6(9):e24374 (2011).
Shigefumi Maesaki, "Drug Delivery System of Anti-Fungal and Parasitic Agents," Current Pharmaceutical Design, 8(6):433-440 (2002).
Romberg et al., "Sheddable coatings for long-circulating nanoparticles," Pharm Res. 25(1):55-71 (2008).
Vilaro and Llobera, "Uptake and Metabolism of Intralipid by Rat Liver: An Electron-Microscopic Study," The Journal of Nutrition, 118(8):932-940 (1988).
K.M. Nugent "Intralipid Effects on Reticuloendothelial Function," Journal of Leukocyte Biology 36(2):123-132 (1984).
Jeff Bulte and Dam Kraitchman, "Iron oxide MR contrast agents for molecular and cellular imaging," NMR Biomed. 17(7):484-499 (2004).
Hu et al., "Nanoparticle-assisted combination therapies for effective cancer treatment" Therapeutic Delivery 1(2):323-34 (2010).
L. Zhang et al., "Development of Nanoparticles for Antimicrobial Drug Delivery," Current Medicinal Chemistry, 17(6):585-594 (2010).
Hamed Laroui et al., "Gastrointestinal Delivery of Anti-Inflammatory Nanoparticles," Methods in Enzymology, 509:101-25 (2012).
Barua et al., "Particle shape enhances specificity of antibody-displaying nanparticles," PNAS 110(9):3270-5 (2013).
Yang et al., "Single chain epidermal growth factor receptor antibody conjugated nanoparticles for in vivo tumor targeting and imaging," Small, 5(2):235-43 (2009).
Hu et al., "Assembly of Nanoparticle-Protein Binding Complexes: From Monomers to Ordered Arrays," Angewandte Chem Int. Ed. Engl, 46(27):5111-5114 (2007).
Rodriguez et al., Minimal "Self" peptides that inhibit phagocytic clearance and enhance delivery of nanoparticles, Science 339(6122):971-975 (2013).
Nathaniel L. Rosi et al., "Oligonucleotide-Modified Gold Nanoparticles for Intracellular Gene Regulation," Science 312:1027-1030 (2006).
Yue Zhao et al., "Small-molecule-directed nanoparticle assembly towards stimuli-responsive nanocomposites," Nature Materials, 8(12):979-985 (2009).
Ye Q et al., "In vivo detection of acute rat renal allograft rejection by MRI with USPIO particles," Kidney Int. 61(3):1124-35 (2002).
Wu et al., "In situ labeling of immune cells with iron oxide particles: an approach to detect organ rejection by cellular MRI," PNAS 103(6):1852-1857 (2006).
Wu et al., "Noninvasive evaluation of cardiac allograft rejection by cellular and functional cardiac magnetic resonance," JACC Cardiovasc Imaging, 2(6):731-741 (2009).
Haxton et al., "Polymeric Drug Delivery of Platinum-Based Anticancer Agents," Jul. 2009, Journal of Pharmaceutical Sciences, 98(7):2299-2316.

* cited by examiner

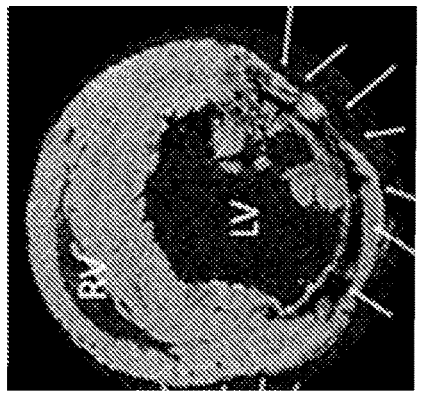 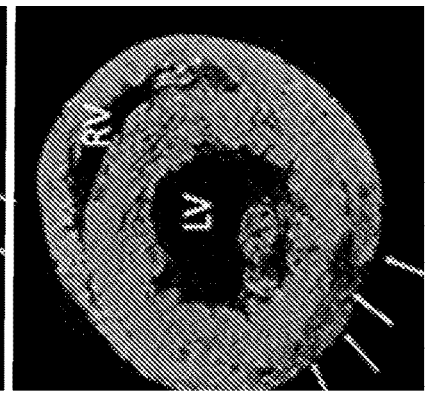
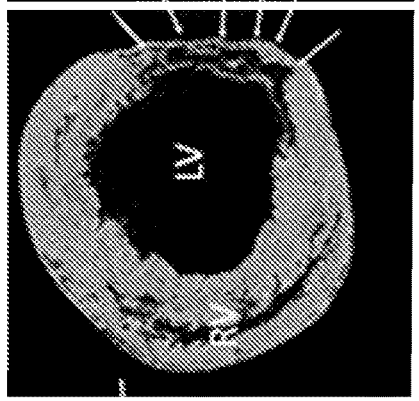 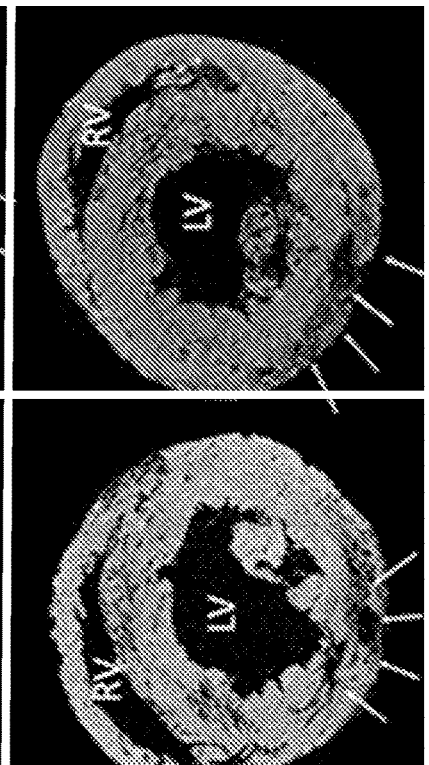
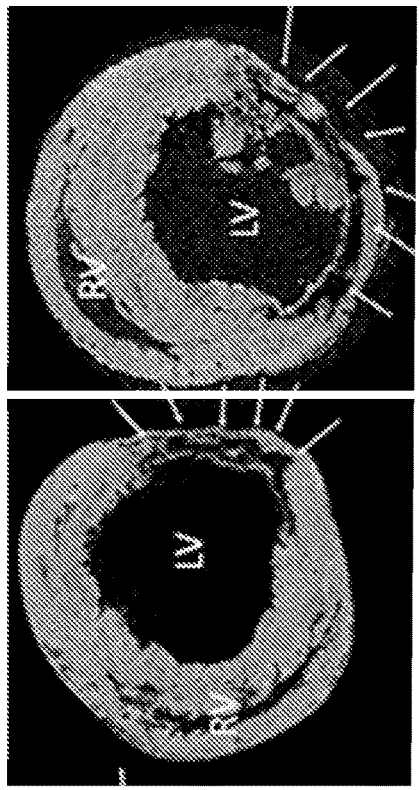 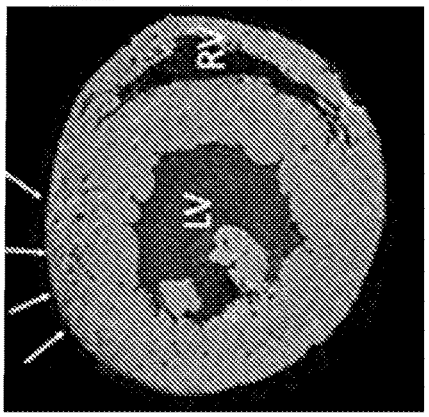
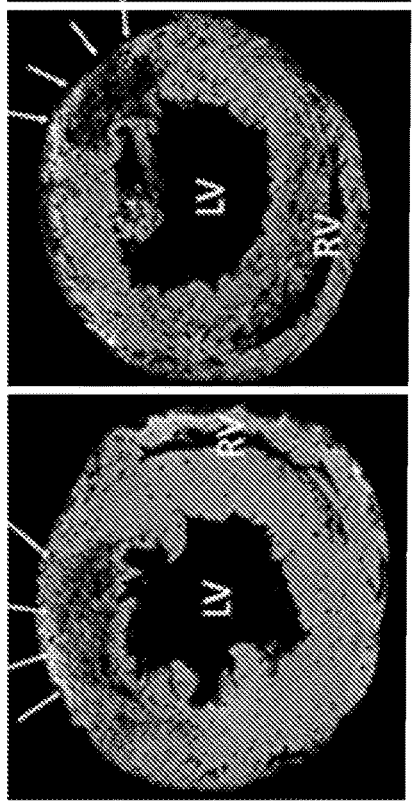
FIG. 2A  FIG. 2B  FIG. 2C  FIG. 2D
FIG. 2E  FIG. 2F  FIG. 2G  FIG. 2H

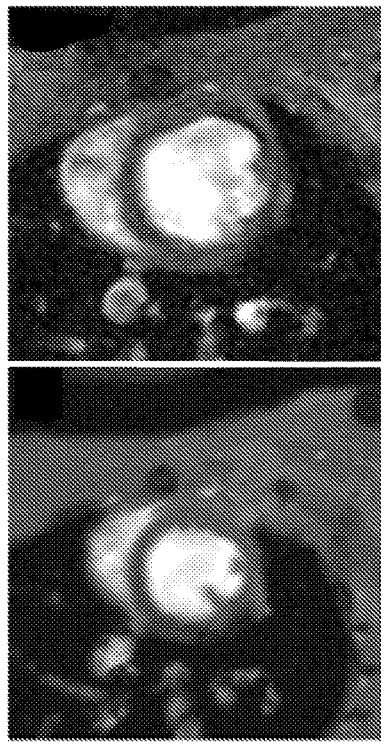
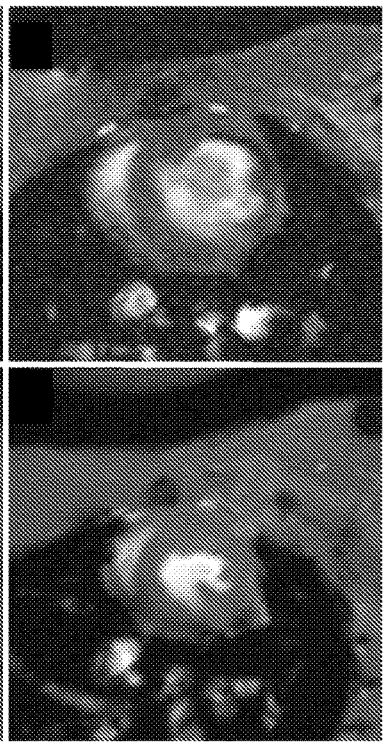
FIG. 3A  FIG. 3B
FIG. 3C  FIG. 3D
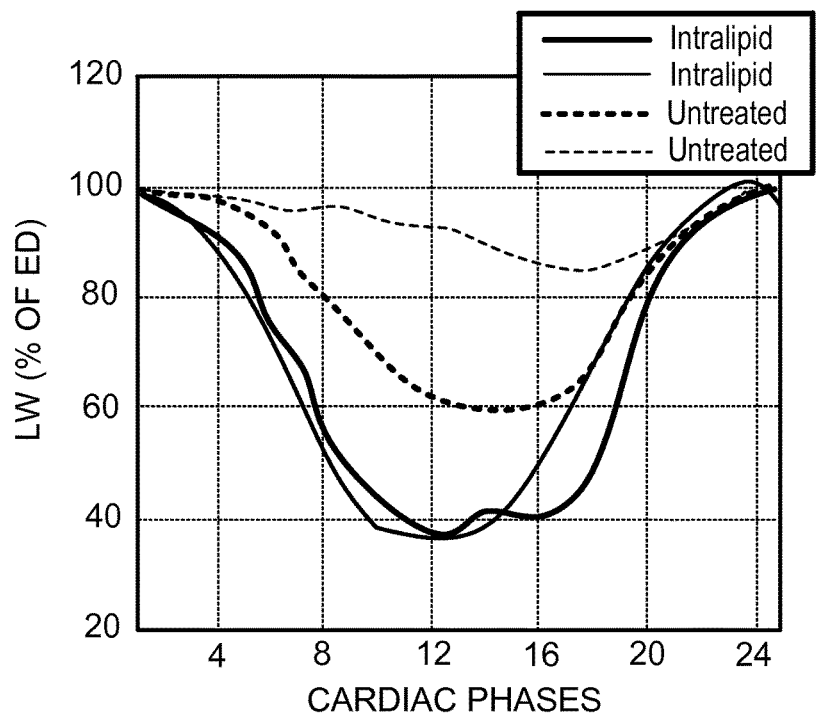
FIG. 3E

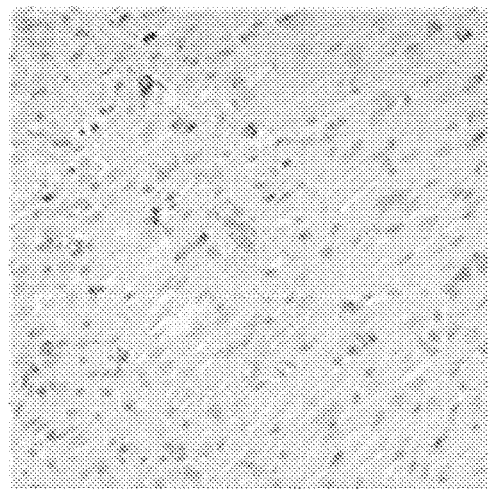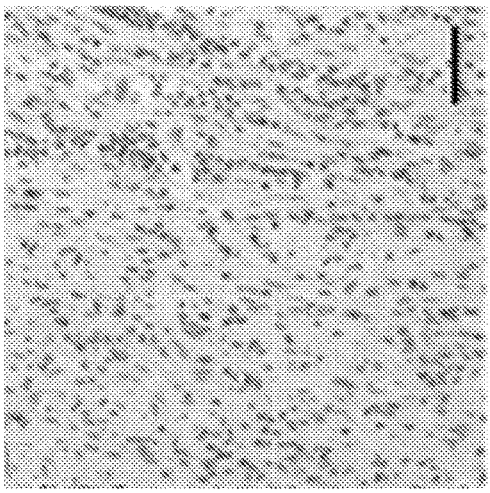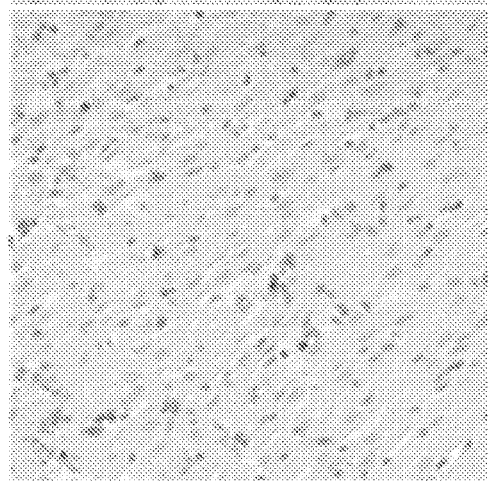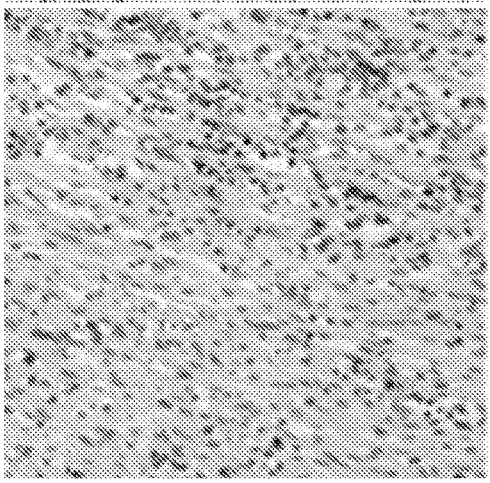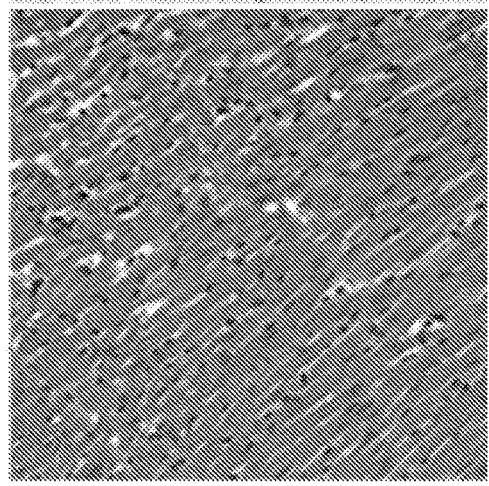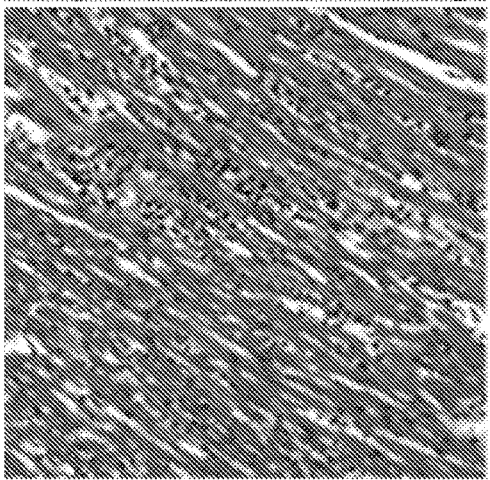

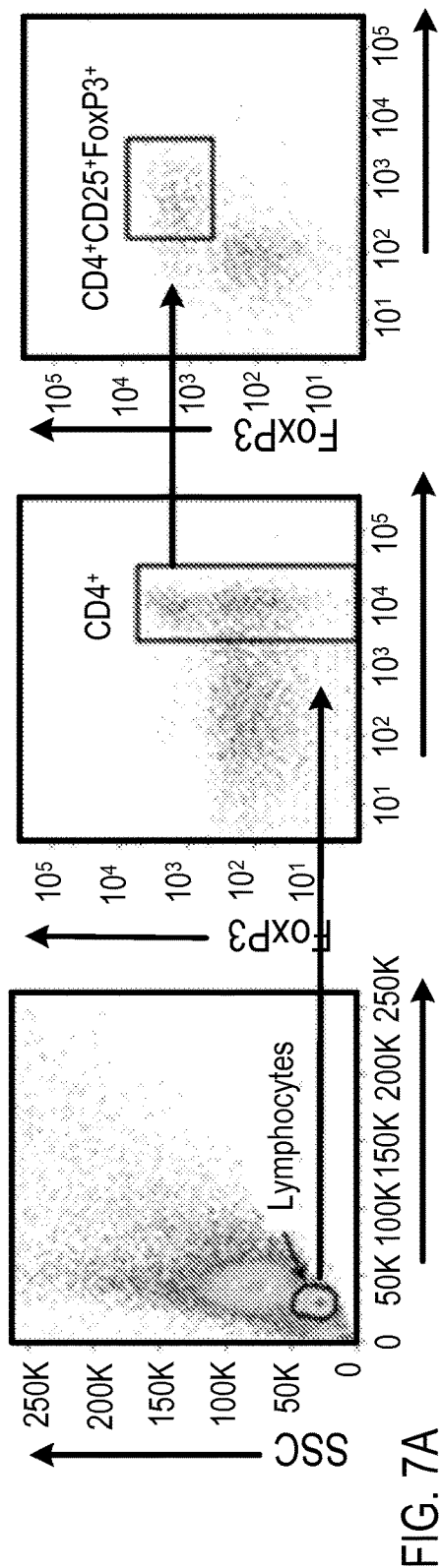
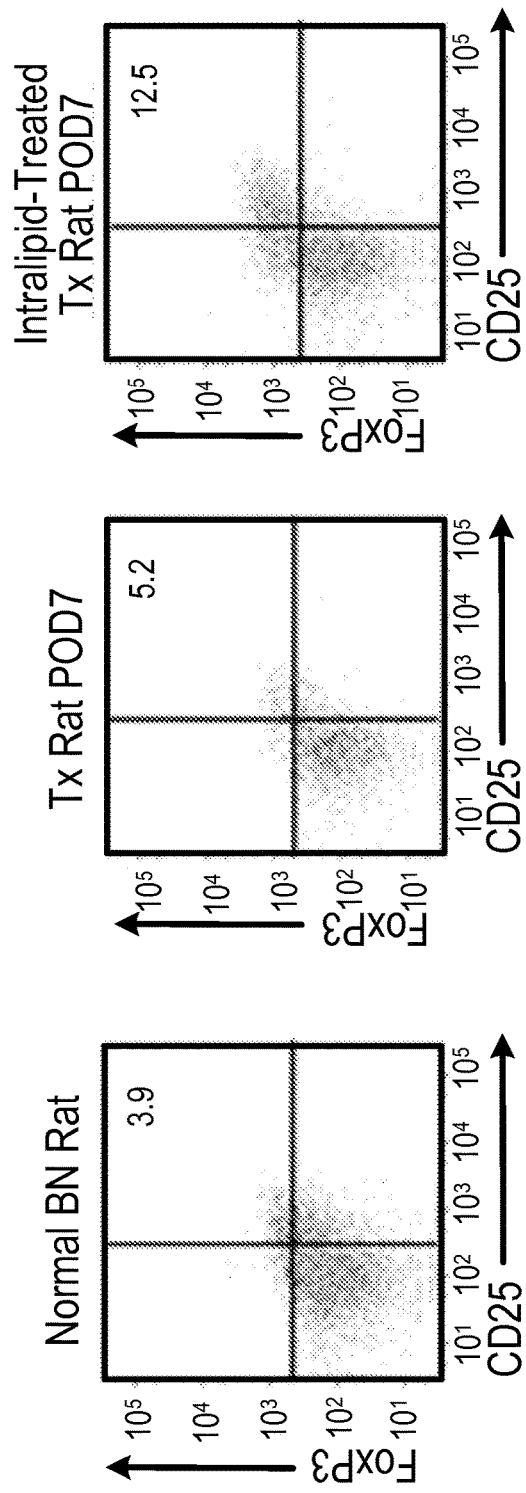
FIG. 7A  FIG. 7B  FIG. 7C  FIG. 7D

METHODS AND MATERIALS FOR REDUCING ORGAN TRANSPLANT REJECTION OR ISCHEMIC/REPERFUSION INJURY IN A SUBJECT

CROSS-REFERENCE TO RELATED APPLICATIONS

This application is a §371 National Stage Application of PCT/US2013/058598, filed Sep. 6, 2013, which, in turn, claims priority to U.S. Application Ser. No. 61/848,127, filed Dec. 20, 2012, the disclosure of which is incorporated by reference in its entirety.

STATEMENT REGARDING FEDERALLY SPONSORED RESEARCH OR DEVELOPMENT

This invention was made with government support under the National Institutes of Health R01HL-081349 and P41EB-001977. The government has certain rights in this invention.

TECHNICAL FIELD

This invention generally relates to methods for reducing organ transplant rejection in a subject, and more particularly to administering a fat emulsion before and/or after the subject undergoes an organ transplant to reduce organ transplant rejection in the subject. This invention also generally relates to methods for minimizing ischemia and ischemia/reperfusion injury in a subject, and more particularly to administering a fat emulsion to the subject before, at the onset of, or after an ischemic event in the subject.

BACKGROUND

Organ transplantation is a therapeutic tool for the treatment of severe organ failure, yet transplant rejection remains a major cause of the graft loss. In addition to organ rejection, ischemia/reperfusion injury (IRI) often accompanies organ transplantation. See, e.g., Lutz, et al., *J. Inflamm.* (Lond), 7:27 (2010). IRI has an influence on not only early post-transplant graft dysfunction, but also the long-term poorer outcomes of a transplanted organ. Moreover, IRI, which has been implicated in heart attack, stroke, traumatic head injury, and during cardiac surgery, is a major burden on individuals and health care systems worldwide. See, e.g., Arumugam, et al., *Shock*, 32:4-16 (2009). For example, ischemic cardiac injury following acute myocardial infarction (AMI) is the leading cause of heart failure and mortality in the United States. See, Heidenreich, et al., *Circulation*, 123:933-944 (2011).

Ischemic myocardial injury occurs in many clinical conditions, such as heart transplantation, cardiac bypass, AMI, and coronary stenting after AMI. See, e.g., Bopassa, *Am. J. Cardiovas. Dis.*, 2:223-236 (2012). The restoration of myocardial perfusion, known as reperfusion, saves the ischemic myocardium, but also can induce a deleterious effect in addition to that of ischemic stress. Subsequent restoration of blood flow in ischemic tissues is often followed by reperfusion injury, which results in increased organ injury. In the case of AMI, occlusion of the coronary artery decreases the delivery of oxygen and of nutrients to segments of the myocardium. Timely treatment of AMI, using angiotensin-converting enzyme (ACE) inhibitors or angiotensin receptor blockers (ARBs) for left ventricular systolic dysfunction (LVSD), aspirin or fibrinolytic to dissolve blood clots, or percutaneous coronary intervention (PCI) to open blockages, has greatly decreased 30-day in-hospital deaths. See e.g., Van de Werf, et al., *Eur. Heart J.*, 29"2909-2945 (2008). However, even with successful blood-flow restoration, IRI often results in tissue damage and adverse remodeling. The rate of developing post-AMI heart failure increases while acute mortality decreases. Similarly, acute kidney IRI is a common and important problem in both native and transplanted kidneys, contributing to both early and late dysfunction of the organs. See, e.g. Kosieradzki and Rowinski, *Transplant Proc.*, 40:3279-3288 (2008).

IRI is a series of events in which one event triggers the next. See, e.g., Chan, et al., *Br. J. Surg.*, 90:1470-1478 (2003). Thus "ischemic cascade" is actually a misnomer, since events are not always linear: in some cases they are circular, and sometimes one event can cause or be caused by multiple events. In addition, cells receiving different amounts of blood may go through different chemical processes. A growing body of literature suggests that both innate and adaptive immune responses play crucial roles in regulating the inflammation and the subsequent wound healing response. See, e.g., Epelman and Mann, *J. Cardiovas. Transl. Res.*, 5(6):827-3 (2012). The IRI cascade usually goes on for two to three hours, but can last for days, even after normal blood flow returns. There are still no specific treatments for IRI insults. Thus, there is a need for therapeutic agents that can be used in patients to can protect organs against IRI and against organ transplant rejection.

SUMMARY

The present document is based, at least in part, on methods for reducing organ transplant rejection in a subject (e.g., a human subject) by administering a fat emulsion before and/or after the organ transplant. The methods described herein can, for example, reduce transplant rejection by, for example, reducing immune cell infiltration, increasing the number of regulatory T cells in the peripheral immune system, preserving tissue integrity and/or improving transplant survival in the subject.

The present document also is based, at least in part, on methods for minimizing ischemic or ischemia/reperfusion injury in a subject (e.g., a human subject) by administering a fat emulsion to the subject before, at the onset of, or after an ischemic event in the subject. The methods described herein, can minimize ischemic or ischemic/reperfusion injury by, for example, protecting tissue, reducing inflammation, increasing the number of regulatory T cells in the peripheral immune system and organ, and improving organ function.

In one aspect, this document features a method of reducing organ transplant rejection in a human subject. The method comprises administering a fat emulsion to the subject before the subject undergoes an organ transplant, wherein the fat emulsion is administered between 0 hours and 24 hours before the organ transplantation. For example, the fat emulsion can be administered 0.3 and 4 hours, 0.3 and 3 hours, 0.5 and 1.5 hours, 4 and 10 hours, 10 and 24 hours, or 10 and 15 hours before the organ transplantation. The fat emulsion can be administered one hour before the organ transplantation. The fat emulsion can be administered intravenously to the subject.

In one aspect, this document features a method of reducing organ transplant rejection in a human subject. The method includes administering a fat emulsion to the subject after the subject undergoes an organ transplant, wherein the fat emulsion is administered between 0 hours and 24 hours after the organ transplantation. For example, the fat emulsion can be administered 0.3 and 4 hours, 0.3 and 3 hours, 0.5 and 1.5 hours, 4 and 10 hours, 10 and 24 hours, or 10 and 15 hours after the organ transplantation. The fat emulsion can be administered one hour after the organ transplantation. The fat emulsion can be administered intravenously to the subject.

In any of the methods described herein, the organ transplant can be a heart transplant, kidney transplant, liver transplant, lung transplant, or pancreas transplant.

This document also features a method of minimizing ischemia or ischemia/reperfusion injury in a subject. The method comprises administering a fat emulsion to the subject before, at the onset of, or after an ischemic event in the subject. The ischemic event can be a surgical procedure such as cardiac bypass or coronary stenting, or an event such as a myocardial infarction or a stroke. The fat emulsion can be administered at the onset of the ischemic event. The fat emulsion can be administered after the ischemic event (e.g., 2 hours and 120 hours after the onset of the ischemic event). The fat emulsion can be administered before the ischemic event (e.g., between 0 and 24 hours, 0.3 and 4 hours, 0.3 and 3 hours, 0.5 and 1.5 hours, 4 and 10 hours, 10 and 24 hours, or 10 and 15 hours before the ischemic event).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIG. 2A-2H depict ex-vivo magnetic resonance microscopy (MRM) at 11.7-Tesla of hearts harvested 2 days (A, B, E, F), 1 week (C, G), and 2 weeks (D, H) after a 45-min transient ischemic injury of untreated animals (A to D) or Intralipid®-treated animals (E to H). White arrows point to spots with hypointensity, which are mainly MPIO-labeled macrophages. LV refers to left ventricle and RV refers to right ventricle.

FIGS. 3A-3D depict in-vivo cine MRI of (A, B) untreated and (C, D) Intralipid®-treated ischemic hearts at (A, C) end-diastole and (B, D) end-systole.

FIG. 3E depicts a graph of temporal changes of left ventricle volume (LVV) of 2 untreated animals (dotted lines) and 2 treated animals (solid lines) across different cardiac phases through a cardiac cycle.

FIGS. 5A-5F depict photomicrographs of myocardium tissue in a heterotopic heart transplantation model. The myocardium tissue integrity is largely maintained in the Intralipid®-treated group (FIG. 5A) compared with that of the untreated group (FIG. 5D) as revealed by hematoxylin and eosin (H&E) staining FIGS. 5B and 5C correspond with the Intralipid®-treated allograft heart; FIGS. 5E and 5F represent untreated controls. Both innate and adaptive immune responses were attenuated as there were markedly reduced numbers of ED1$^+$ cells (mainly monocytes/macrophages, compare FIGS. 5B and 5E) and CD3$^+$ cells (T-cells, compare FIGS. 5C and 5F) in the Intralipid®-treated allograft heart. Graft samples were obtained on post operating day (POD) 7. Scale bar represents 100 μm.

FIGS. 7A-7D depict that Intralipid® increases the number of CD4$^+$CD25$^+$Foxp3$^+$ regulatory T cells (Tregs) in the peripheral blood of allograft recipients. FIG. 7A depicts the gating strategy used for the determination of Tregs in peripheral blood. FIGS. 7B-7D depict the percentage of Tregs out of total CD4$^+$ T-cells in the blood of normal Brown Norway (BN) rats (FIG. 7B), untreated recipients (FIG. 7C, POD 7), and Intralipid®-treated recipients (FIG. 7D, POD 7).

DETAILED DESCRIPTION

Figure 1A:
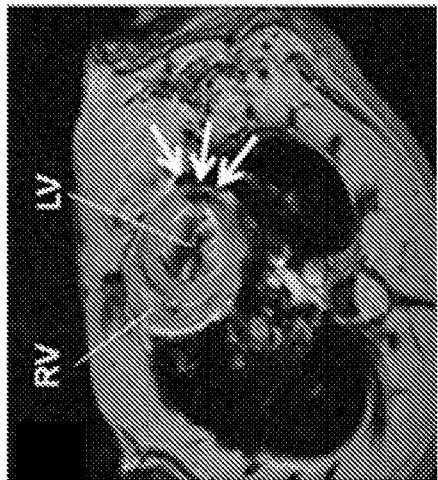
FIGS. 1A-1F depict in-vivo cellular magnetic resonance imaging (MRI) at 7-Tesla of hearts two days after a 45-min transient ischemic injury with in-vivo micron-sized paramagnetic iron-oxide (MPIO) labeling of untreated animals (FIGS. 1A-1C) and Intralipid®-treated animals (FIGS. 1D-1F). White arrowheads point to the areas with hypointensity, the result of infiltrating MPIO-labeled macrophages, which coincide with areas with IRI. LV refers to left ventricle and RV refers to right ventricle.
Figure 1B:
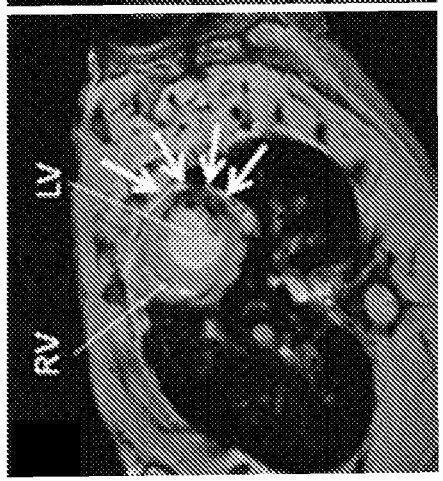
Figure 1C:
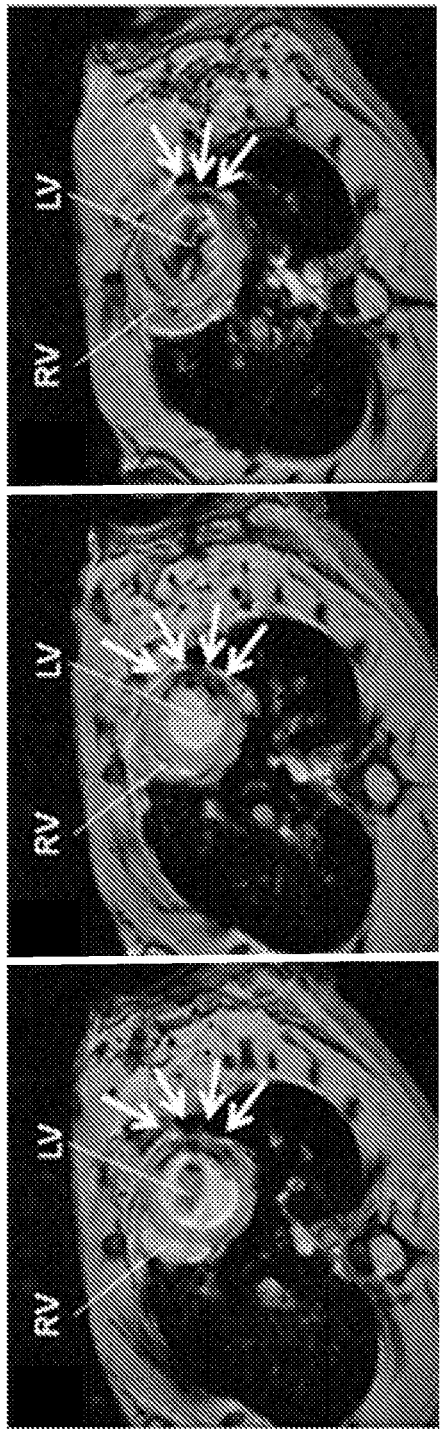
Figure 1D:
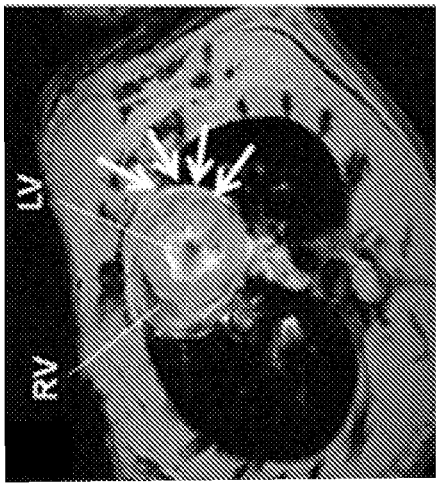
Figure 1E:
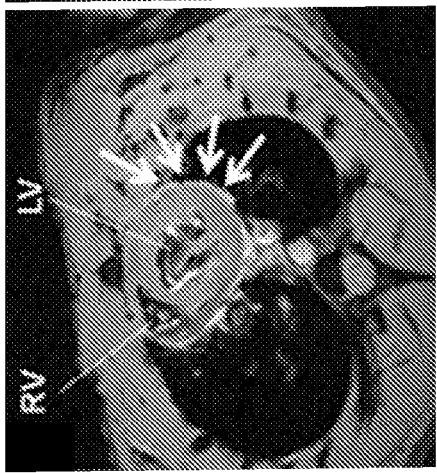
Figure 1F:
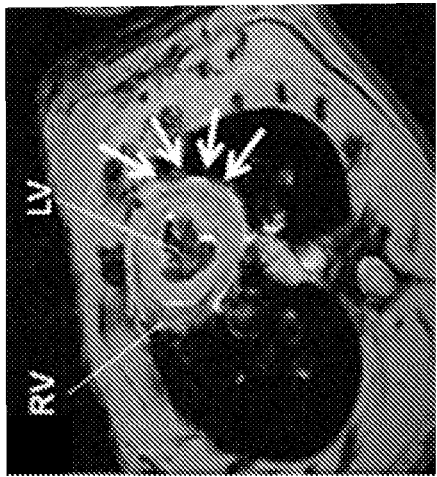
Figure 1G:
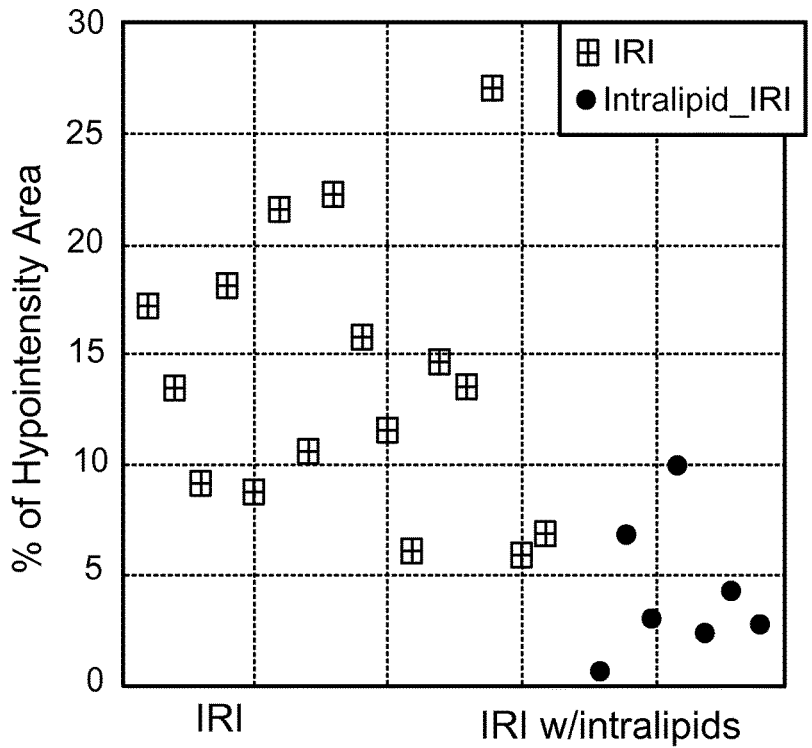
FIGS. 1G and 1H depict plots of the percent area of myocardium with image hypointensity (infiltration area) for untreated (hatched box or bar) and Intralipid®-treated (solid circle or bar) IRI animals.
Figure 1H:
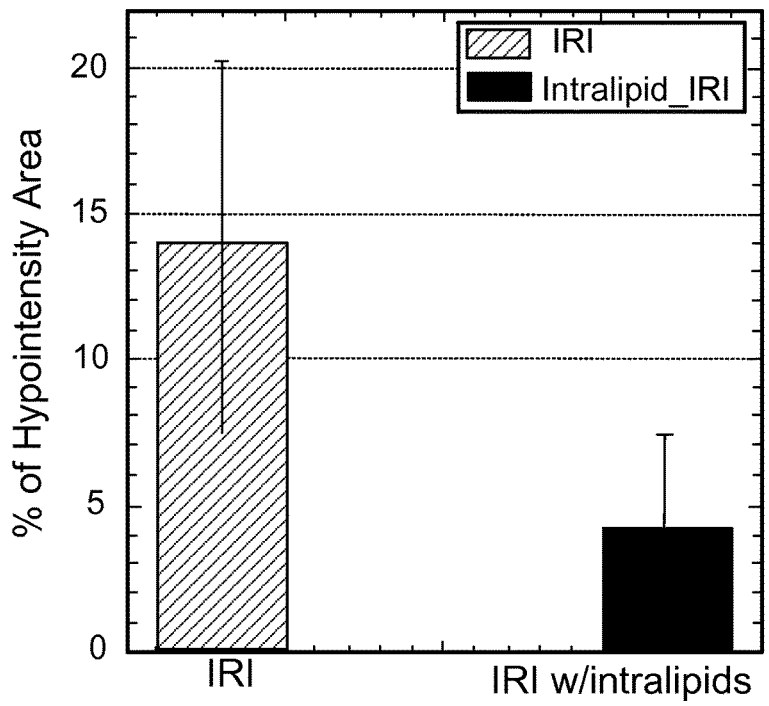
Figure 4A:
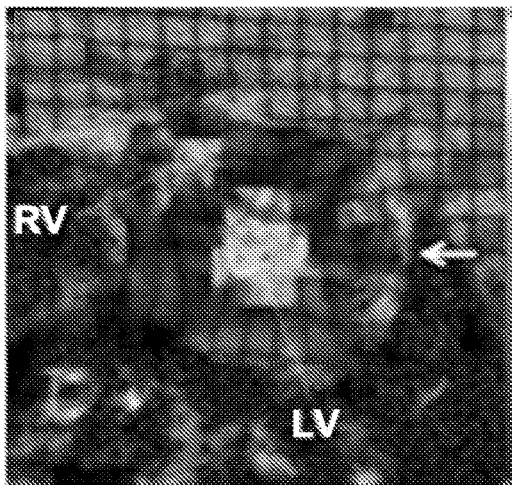
FIGS. 4A and 4B depict circumferential strain (Ecc) map, derived from tagging MRI of an un-treated heart (FIG. 4A) and an Intralipid®-treated heart (FIG. 4B), which had undergone a 45-min transient ischemic injury. The sites of ischemic injury are indicated with white arrowheads.
Figure 4B:
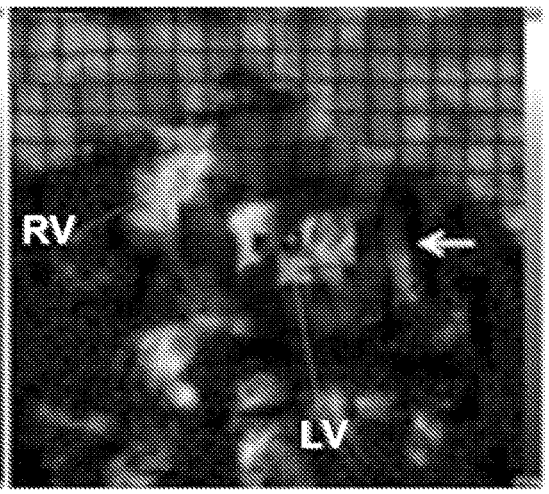
Figure 4C:
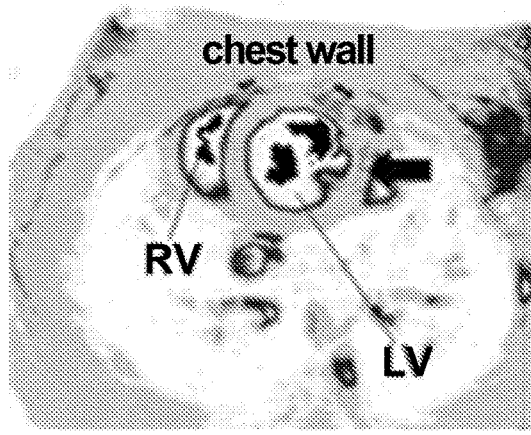
FIGS. 4C and 4D depict first-pass perfusion with bolus gadolinium (Gd) administration of an untreated IRI heart (FIG. 4C) and an Intralipid®-treated IRI heart (FIG. 4D). The sites of ischemic injury are indicated with arrowheads.
Figure 4D:
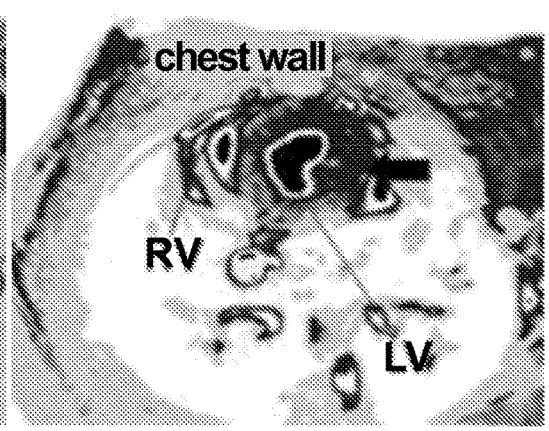

This document provides methods and materials for decreasing organ transplant rejection and/or minimizing ischemia or ischemia/reperfusion injury in a subject (e.g., a mammalian subject such as a human or other non-human primate, a rat, guinea pig, mouse, or a farm animal such as a pig, sheep, goat, horse, or cow).

The methods and materials described herein include administering a fat emulsion to a subject up to about 24 hours before and/or after the organ transplant or before, at the onset of, or after the onset of an ischemic event in the subject. For example, as described herein, administering a fat emulsion to a subject before the subject receives an organ transplant can help reduce transplant rejection by protecting the transplant against rejection, reducing inflammation, preserving tissue integrity, improving organ function, improving graft survival, and/or increasing the number of CD4$^+$ CD25⁺Foxp3⁺ regulatory T cells (Tregs) in the peripheral blood of the subject as compared to that in a corresponding subject receiving a corresponding organ transplant without preadministration of the fat emulsion. Reducing transplant rejection can include reducing the severity of the rejection and/or delaying the onset of transplant rejection. The organ transplant can be a heart, kidney, lung, liver, or pancreas transplant, or any other organ that is suitable for transplantation. Generally, in humans, most organ transplantations are allografts, i.e., from a genetically non-identical member of the same species.

For example, as described herein, administering a fat emulsion to a subject before, at the onset of, or after an ischemic event can minimize ischemia or ischemia/reperfusion injury by reducing inflammation, preserving organ function (e.g., cardiac or renal function), and reducing ischemic tissue damage and reperfusion injury as compared to that in a corresponding subject having a corresponding ischemic event without administration of the fat emulsion before, at the onset of, or after the ischemic event. Ischemia is an event caused by insufficient blood supply to the tissue, resulting in starvation of oxygen, metabolic waste and toxic radical build-up, and ultimately cell death and tissue damage. Restoration of the blood flow can cause additional damage to the tissue, known as reperfusion injury. Ischemic and reperfusion events can occur in organs such as the heart, brain, kidneys, or bowels; in limbs such as arm, hands, legs, or feet; or can be due to a surgical procedure (e.g., cardiac bypass, valve replacement, or coronary stenting). Cardiac ischemic events can be caused, for example, by coronary artery disease, resulting in myocardial infarction, which can lead to subsequent heart failure, depending on the extent of the ischemic injury. Brain ischemic events include acute, chronic, or transient ischemic strokes. Ischemic reperfusion injury can occur during or as a result of organ transplant surgery, where the blood flow in the donor organs is cut off for a period of time and then later restored.

In the methods described herein, an amount of fat emulsion effective to reduce organ transplant rejection and/or minimize ischemia or ischemia/reperfusion injury is administered to the subject. As used herein, the term "effective amount" refers to an amount (or amounts) of a fat emulsion that decreases organ transplant rejection and/or minimizes ischemia or ischemia/reperfusion injury without inducing significant toxicity to the host. For example, an effective amount of fat emulsion can range from, for example, about 0.1 g of fat emulsion/kg of body weight (mg/kg) to about 4 g/kg (e.g., 0.5 to 1.0, 0.75 to 1.5, 1 to 3, 1 to 4, 1.5 to 3, 1.5 to 4, 2 to 4, 1, 1.5, 2, 2.5, 3, 3.5, or 4 mg/kg). An effective amount of fat emulsion as well as frequency and duration of administration can be determined by a physician, taking into account various factors that can modify the action of drugs such as overall health status, body weight, sex, diet, time and route of administration, other medications, and any other relevant clinical factors.

While in some embodiments, a single treatment (e.g., a single intravenous administration) of fat emulsion is sufficient to decrease organ transplant rejection and/or minimize ischemia or ischemia/reperfusion injury in the subject, in some embodiments, treatment can comprise multiple administrations of the fat emulsion at various intervals and over different periods of time as required.

In some embodiments, the fat emulsion is administered between 0 hours and 24 hours before an organ transplant or an ischemic event. For example, the fat emulsion can be administered between 0.1 and 24 hours, 0.1 and 20 hours, 0.1 and 16 hours, 0.1 and 15 hours, 0.1 and 10 hours, 0.1 and 5 hours, 0.1 and 2.5 hours, 0.2 and 24 hours, 0.2 and 20 hours, 0.2 and 15 hours, 0.2 and 10 hours, 0.2 and 5 hours, 0.2 and 2.5 hours, 0.3 and 4.5 hours, 0.3 and 4 hours, 0.3 and 3 hours, 0.5 and 24 hours, 0.5 and 20 hours, 0.5 and 15 hours, 0.5 and 10 hours, 0.5 and 5 hours, 0.5 and 3.5 hours, 0.5 and 2 hours, 0.5 and 1.5, 1 and 24 hours, 1 and 15 hours, 1 and 10 hours, 1 and 5 hours, 1 and 3 hours, 1 and 2.5 hours, 1 and 1.5 hours, 2 and 24 hours, 2 and 20 hours, 2 and 15 hours, 2 and 10 hours, 2 and 5 hours, 5 and 24 hours, 5 and 20 hours, 5 and 15 hours, 5 and 10 hours, 10 and 24 hours, 10 and 20 hours, or 10 and 15 hours before or after the organ transplant. In some embodiments, the fat emulsion is administered about 1 hour before the organ transplant or ischemic event.

In some embodiments, the fat emulsion is administered at the onset of an ischemic event. As used herein, the term "onset" refers to the period up to about 1 hour (e.g., 10 to 60 minutes, 10 to 50 minutes, 20 to 60 minutes, 20 to 40 minutes, 30 to 50 minutes. or 30 to 60 minutes) after symptoms of the ischemic event are observed. For example, for a stroke, symptoms of the ischemic event can include paralysis or numbness of the face, arms or legs, speech abnormalities, or vision difficulties. Symptoms of a myocardial infarction can include chest pain, shortness of breath, palpitations, or undue fatigue.

In some embodiments, the fat emulsion is administered after the organ transplant or after the onset of the ischemic event, e.g., at least 2, 4, 6, 10, 12, 24, 48, 72, or 120 hours after the organ transplant or onset of symptoms of the ischemic event. As described herein, Intralipid® treatment post-coronary artery occlusion effectively rescues the heart from IRI, leading to reduced inflammatory cell infiltration and preserved morphologic architecture. In addition, as described herein with an acute kidney IRI model, it was found that both pre- and post-conditional Intralipid® treatments are beneficial in not only reducing IRI damage, but also in improving kidney function. Using a kidney transplant model, it was found that Intralipid®-treated allografts show less prominent interstitial and tubular edema. Using a heart transplant model, a dramatic reduction in the numbers of infiltrating macrophages and T-cells were observed in allografts of Intralipid®-treated transplant recipients. In both transplant models, allografts show reduced inflammation and improved function as well as increased graft survival with Intralipid® treatment. An increased number of Tregs in the blood of heart transplant recipients was found.

In embodiments in which the fat emulsion is administered multiple times (e.g., two, three, four, or more times), at least one of the administrations is between 0 hours and 5 hours before the organ transplant or onset of the ischemic event. In some embodiments, multiple administrations of the fat emulsion occur between 0 hours and 24 hours before or after the organ transplant or ischemic event.

The fat emulsion can be formulated for administration by any route, including, without limitation, oral or parenteral routes of administration such as intravenous, intramuscular, intraperitoneal, subcutaneous, intrathecal, intraarterial, or nasal. Typically, the fat emulsion is administered intravenously.

In some embodiments, the fat emulsion comprises one or more of soybean oil or other vegetable oil, fish oil, phospholipids (e.g., egg yolk phospholipids), and glycerol or other pharmaceutically acceptable carrier, or combinations and subcombinations of the foregoing. Intralipid® is a particularly useful fat emulsion. Intralipid® was approved by U.S. FDA in 1972 as a source of parenteral nutrition for patients. Intralipid® also has been used clinically to intravenously provide nutrition for patients and to also reverse propanolol toxicity (Harvery and Cave, *J. Med. Toxicol.*, 4:71-76 (2008)). Intralipid® also affects immune modulation (see Wanten and Calder, *Am. J. Clin. Nutr.*, 85:1171-1184 (2007); and Edwards, et al., *J. Lipid Res.*, 53:1979-1986 (2012)). Short-term Intralipid® infusion can blunt the inflammatory response to endotoxin (Krogh-Madsen, et al., *Am J. Phsiol. Endocrinol. Metab.*, 294:E371-379 (2008)). Clinically, patients tolerate Intralipid® well when it is administered according to guidelines. Intralipid® 20% is composed of 20% soybean oil, 1.2% egg-yolk phospholipids, and 2.25% glycerol. Other Intralipid® formulations include Intralipid® 10% and Intralipid® 30%. Kupffer cells in the liver play an important role in the uptake and metabolism of Intralipid. See, for example, Vilaro and Llobera, *J Nutr.*, 118:932-940 (1988). Without being bound to a particular mechanism, Intralipid® may protect organs against IRI insults and reduce solid transplant rejection by modulating the immune system, in part, through regulating the immunosuppressive regulatory T cells during IRI and organ rejection.

In some embodiments, the methods described herein further comprise monitoring the subject after the organ transplantation or ischemic event to assess, for example, organ function (e.g., cardiac function), graft stability, or inflammation in the subject. Methods such as multi-parameter magnetic resonance imaging (MRI), flow cytometry, magnetic resonance microscopy (MRM), histopathology, fluorescence microscopy, and blood chemistry tests can be used to monitor the subject.

In some embodiments, monitoring the subject can include administering particles and using an imaging method (e.g., MRI) to label or track cells (e.g., immune cells such as monocytes and macrophages), determine location of the particles, detect any structural abnormalities within the subject, or distinguish between pathologic and normal tissue. Such methods can be performed with particles of any size (e.g., nano- or micron sized) and of any material suitable for administration to the subject and useful for imaging. For example, the particles can be silica oxide particles, metal oxide particles such as zinc, aluminum, or iron oxide particles, superparamagnetic iron platinum particles, gadolinium particles, manganese particles, gold particles, silver particles, lipid particles, polyacrylic acid particles, or polymer particles. In some embodiments, the particles are iron oxide particles such as superparamagnetic iron oxide particles (e.g., ultrasmall superparamagnetic iron oxide particles (USPIO) or micron sized superparamagnetic iron oxide particles (MPIO)). The particles can be neutral, zwitterionic, negatively, or positively charged. In addition, in some embodiments, the surfaces of the particles are coated, for example, with a dextran, a dendrimer (e.g., a carboxylated dendrimer), styrene/divinyl benzene, or vinyl polymer, or modified, for example, with a liposome, or polyethylene glycol (PEG) or other polyether. See, e.g., Bulte and Kraitchman, *NMR Biomed.*, 17:484-499 (2004).

In embodiments in which particles are administered to the subject, the particles are administered 1 to 3 days before the organ transplant or ischemic event, or 1 day to 1 month after the organ transplant or ischemic event. The dosage of particles to be administered to the subject can be determined by a physician, taking into account various factors that can modify the action of drugs such as overall health status, body weight, sex, diet, time and route of administration, other medications, and any other relevant clinical factors. Typical dosages of USPIO for imaging methods can range from 4.5 to 15 mg/kg. Typical dosages of MPIO for imaging methods can range from 4.5 to 18 mg/kg.

The invention will be further described in the following examples, which do not limit the scope of the invention described in the claims.

EXAMPLES

Example 1

Methods and Materials

Animals—All animals used in this study were male inbred Brown Norway (BN; RT1$^n$) and Dark Agouti (DA; RT1$^a$) rats obtained from Harlan (Indianapolis, Ind.) having body weights between 180-260 grams each. All experiments involving animal subjects were approved by the Institutional Animal Care and Use Committee of Carnegie Mellon University. Animal care was provided in accordance with the Guide for the Care and Use of Laboratory Animals (Eight Edition, 2011). Rats undergoing surgical procedure were intubated and ventilated with 2% isoflurane in a 2:1 $O_2:N_2O$ gas mixture at 1.0 mL/100 g body weight and 60 bpm.

Renal Artery Occlusion Model—Acute kidney IRI was induced in 10 to 12 week old BN rats. In brief, a middle abdominal incision was made and bilateral renal pedicles were clamped for 45 min under general anesthesia. After unclamping, the restoration of renal blood flow was confirmed and the incision closed. Five rats in each group were treated with either Intralipid® or PBS at various time points of 30 min, and 1, 2, 4, 24, and 48 hrs after reperfusion. Twenty-four hrs after reperfusion, 0.5 ml of blood was drawn every other day up to 10 days. Urine samples were collected before and at the endpoint of the experiment to measure the serum level of blood urea nitrogen (BUN) and creatinine At the endpoint of the experiment on post-operating day (POD) 10, both the right and left kidneys were harvested for cytokine analysis and pathological examination.

Heart Coronary Artery Occlusion Model—The rat heart IRI model was employed with a 45-min transient left anterior descending (LAD) coronary artery ligation, followed by reperfusion. For the pre-conditioned treatment study, 40 male BN rats were subjected to an ischemia procedure in which 18 animals were given Intralipid® intravenously one hour prior to and at the onset of the ischemia, and 22 animals received no Intralipid®. Additionally, six sham animals were subjected to the same open chest surgical procedure. For the post-conditional treatment study, rat heart IRI was induced in 10 to 12 week old BN rats, with a 45-min transient LAD coronary artery ligation with 7-0 nylon suture (Sherwood Medical, St. Louis, Mo., USA), followed by reperfusion. Five rats in each group were treated with Intralipid® (treated groups) or phosphate-buffered-saline (PBS) (control groups) at various time points following reperfusion. Intralipid® (Intralipid® 20.0%, Fresenius Kabi, Bad Homburg, Germany) was intravenously administered at a dose of 2 g/kg for all rats.

In-Vivo MRI—In vivo MRI was performed on a Bruker AVANCE 7-Tesla/21-cm system using a 72-mm birdcage coil. Rats were intubated and ventilated with 2% isoflurane in a 2:1 $O_2:N_2O$ gas mixture at 1.0 mL/100 g body weight and 60 bpm. Rectal temperature was maintained at 36.5±1° C. with warm air and subcutaneous needle electrodes were placed on the abdomen to detect electrocardiography (ECG) of the transplanted heart (SA Instruments, Stony Brook, N.Y.). Cellular MRI was conducted to non-invasively monitor the inflammation status of the myocardium after onset of IRI. Inflammatory cells were labeled in circulation by intravenous administration of MPIO particles, and the infiltration of MPIO-labeled cells (mainly macrophages/monocytes) into the heart was detected by in-vivo $T_2^*$-weighted MRI. Ten short-axis slices were used to cover the entire volume of the heart for $T_2^*$-weighted imaging using the following parameters: repetition time (TR)=one cardiac cycle (~180 ms); echo time (TE)=3.2 ms for tagging MRI, and 6 to 10 ms for $T_2^*$-weighted imaging; field of view (FOV)=3-4 cm, with 117- to 156-µm in-plane resolution.

Heart Transplantation Model—DA to BN (allogeneic transplant) and BN to BN (syngeneic transplant) rat heterotopic working heart transplantations (Wu, et al., *Method Enzymol.*, 386:73-105 (2004)) were conducted in 10 to 12 week old rats. In brief, the superior vena cava (SVC) of the graft heart was anastomosed to the recipient inferior vena cava (IVC) for keeping pulmonary circulation, and the aorta of the graft heart was anastomosed to the recipient abdominal aorta, and the recipient proximal IVC was partially obstructed to increase volume loading. The total ischemic time for heart graft was around 40 min. Five rats in each group were treated with either Intralipid® or PBS at various time points of 30 min, and 1, 2, 4, 24, 48, 72, and 96 hrs after unclamping.

Kidney Transplant Model—DA to BN (allogeneic transplant) and BN to BN (syngeneic transplant) rat orthotopic kidney transplantation models (Ye, et al., *Kidney Int.*, 61:1124-1135 (2002)) were employed in this study. In brief, after nephrectomy on the left side of the recipient, the graft renal artery and vein were anastomosed end-to-side with the recipient abdominal aorta and inferior vena cava, and a non-splinted end-to-end ureteric anastomosis was carried out with four interrupted stitches using 10-0 nylon suture (Sherwood Medical, St. Louis, Mo., USA). The total ischemic time for kidney graft was around 30 min. The recipient right kidney was kept intact as an internal control for MRI measurements. Five rats in each group were treated with either Intralipid® or PBS at various time points of 30 min, and 1, 2, 4, 24, and 48 hrs after unclamping. In additional sets of experiments, both native kidneys of recipients (n=6) were removed at the time of kidney transplantation, and the recipients were followed for 10 days to assess renal graft function and animal survival.

At the endpoints of the experiments, hearts, kidneys, and various peripherally lymph tissues/organs were harvested for MRM and histopathology examinations. Samples were fixed in 4% paraformaldehyde (PFA), or snap-frozen and stored at −80° C.

Ex-Vivo MRM—Fixed hearts and kidneys were imaged on a Bruker AVANCE DRX 11.7-Tesla system with a Micro2.5 gradient insert. High-resolution 3D images were acquired with the following parameters: TR=350 to 500 ms; TE=5.5 ms, and isotropic resolution=40 µm.

Assessment of Heart Function—Global systolic cardiac function anatomical changes and wall thinning were evaluated with cine MRI over time. Regional wall motion and strains were assessed by tagging MRI followed by strain analysis using HARP software from Diagnosoft, Inc. Myocardial perfusion and infarction were measured by first-pass dynamic with a single bolus of Gd (Omniscan, 0.5 mmol/kg) as well as late gadolinium enhancement (LGE).

Assessment of Renal Function—Urine and plasma samples were analyzed with a creatinine enzymatic assay kit (BioVision Technologies, Mountain View, Calif.) according to the manufacturer's instructions.

Heart and Kidney Digestions—The local immune process during IRI and rejection was further elucidated by analysis of objective tissues. Heart and kidney digestions were performed to quantify inflammatory cells. At the endpoint of the experiment, hearts and kidneys were fragmented using a scalpel into ice-cold RPMI 1640 media immediately after perfusion. The tissue was resuspended in 2-ml RPMI-1640 containing 1.6 mg/ml collagenase B and 100 µg/ml DNAse I (both from Roche Applied Science, Penzberg, Germany), and incubated at 37° C. for 45 min. Cells were pelleted and resuspended in RPMI-1640 with 100 µg/ml of DNAse I alone for a further 15 min at room temperature. Cell samples were centrifuged, resuspended, and passed through a 40-µm cell strainer. Red blood cells were lysed by incubation on ice with ammonium chloride lysis buffer for 5 min. Cells were pelleted and resuspended in 1-ml Dulbecco's PBS (without $Ca^{2+}/Mg^{2+}$) for counting on a hemocytometer before flow cytometry analysis.

Flow Cytometry—Fluorescence-activated cell sorting (FACS, FACSVantage, Becton Dickinson) was used to determine the percentage of monocytes/macrophages, lymphocytes, and NK cells in peripheral blood, heart, kidney, and lymphatic tissues. The cells were stained with following antibodies purchased from AbD Serotec (Oxford, UK): Anti-FoxP3; anti-rat ED1; anti-rat CD3, CD4, CD8; anti-rat major histocompatibility complex class II (MHC class II); and anti-rat NK. Anti-rat CD25 was purchased from eBioscience (San Diego, Calif.). Sample acquisition was terminated after at least 5000 bead-events had been counted. The data are processed with the FlowJo software (Tree Star, Inc, Ashland, Oreg.).

Pathological Studies—Hearts and kidneys wee sent to the Transplantation Pathology Laboratory of the University of Pittsburgh Medical Center for independent and blinded histological analysis. Tissues sections (5 µm) were subjected to H&E staining and immunohistochemical staining with the following mouse anti-rat antibodies: anti-CD3; anti-ED1; anti-MHC Class II (AbD Serotec) for detecting T-cells, macrophages, and antigen presenting cells (APC), respectively. Terminal deoxynucleotidyl transferase mediated dUTP nick end-labeling (TUNEL) staining was performed with the ProLong® Antifade Kit (Molecular Probes, Eugene, Oreg.) for detection of apoptotic cells in hearts and kidneys. The heart graft rejection grades were determined histopathologically according to the International Society for Heart and Lung Transplantation (ISHLT) criteria (Winter, et al., *J. Heart Lung Transplant*, 17:754-760 (1998); Stewart, et al., *J. Heart Lung Transplant*, 24:1710-1720 (2005)). For kidneys, 20 tubules or glomeruli in each kidney were randomly selected at ×400 magnification, and the renal damage in kidney allografts was scored according to the degrees of glomerulosclerosis. Vascular lesions, tubulointerstitial damage, and inflammatory infiltration were scored from 0 to 3: 0, normal; 1, mild; 2, moderate; and 3, severe; using a grading system as described previously (el Nahas, et al., *Kidney Int.*, 40:29-34 (1991); Velasquez, et al., *Hypertension*, 30:1232-1237 (1997)). The mean renal injury score in each rat was calculated and then the scores were averaged for each group. Inflammatory infiltration and tissue integrity based on the presence of expansion of Bowman's space, interstitial edema, epithelial detachment, and tubular cells casts also were inspected in the rat tissues from the acute kidney IRI model. These morphologic changes were graded using the scoring system for renal injury on a scale of 0 to 3: 0, normal; 1, mild; 2, moderate; and 3, severe (23). The apoptotic index was calculated as the number of TUNEL-positive nuclei per field of view (FOV) at ×400 magnification.

Statistical Analysis—All data were expressed as the mean value±SEM. Statistical comparisons were made by ANOVA. The survival rate of rats from acute kidney IRI model after 45 min of ischemia and 10 days of reperfusion was estimated with the Kaplan-Meier method. P<0.05 was considered statistically significant.

Example 2

Intralipid®-Treated Animals Exhibit Preserved Cardiac Function after Ischemic Insult The results from a heart coronary artery occlusion model (see Example 1) reveal that treatment with Intralipid® can protect heart function and reduce adverse myocardial remodeling against IRI (see FIGS. 1-4). After a 45-min transient LAD coronary artery ligation, blood flow is fully restored but inflammation has already set in. Hypointensity was detected in the IRI site of myocardium (see FIGS. 1A-1C) with in-vivo $T_2$*-weighted MRI, indicating the accumulation of MPIO-labeled macrophages. High-resolution ex-vivo MRM and histological staining confirmed that the hypointensity was due to labeled macrophages (see FIGS. 2A-2D). Animals pretreated with Intralipid®, however, showed a significant reduction in macrophage infiltration (see FIGS. 1D-1H & FIGS. 2E-H), indicating reduced in-situ inflammation with Intralipid® pretreatment. In addition, Intralipid®-treated animals do not exhibit similar myocardial atrophy over time (see FIGS. 2G, 2H) as untreated animals (see FIGS. 2C, 2D). Untreated animals exhibited a significant reduction in wall thickness in the infarct site, the infero-lateral and antero-lateral left ventricle (LV) wall regions; whereas the hearts from Intralipid®-treated animals exhibit preserved wall thickness across the LV.

In Intralipid®-treated animals, cardiac function was preserved after the ischemic insult compared to untreated animals (see, FIGS. 3-4). Intralipid®-treated hearts show preserved stroke volume (SV) and ejection fraction (EF) with cine imaging (FIG. 3), regional wall motion (FIG. 4A, 4B) and myocardial perfusion (FIG. 4C, 4D). Tagging MRI was used to quantify ventricular wall motion while the heart pumps blood. Tagging MRI temporarily tags water spins magnetically in myocardium to mark their physical coordinates in space. Strains are values that quantify the extent of ventricular deformation throughout cardiac phases: stretching/elongation or compression/shortening. Circumferential strain (Ecc) is a class of normal strains in which strain-tensors are tangent to the epicardium surface. After the transient 45 minute ischemic event, the un-treated myocardium with IRI (FIG. 4A) exhibited compromised ventricular wall motion with decreased Ecc. On the other hand, with Intralipid® treatment (FIG. 4B), the myocardium did not show the same degradation in Ecc after the ischemic insult. In the ischemic heart of FIG. 4B, Intralipid® treatment preserved most of the ventricular wall motion, comparable to that of un-treated control hearts. This indicates Intralipid® can protect the heart against IRI.

After the transient ischemic event, the un-treated heart (FIG. 4C) showed compromised myocardial perfusion, a measure of the blood supply to the heart. On the other hand, with Intralipid® treatment (FIG. 4D), the myocardium did not show the same decrease in myocardial perfusion after the ischemic insult. This indicates that Intralipid® helps the heart to preserve better coronary artery circulation after IRI.

Although Intralipid® treatment decreases inflammation in the myocardium at the IRI site, it does not change the immune cell composition in peripheral blood.

Example 3

Intralipid® Protects Grafts Against IRI

Figure 6A:
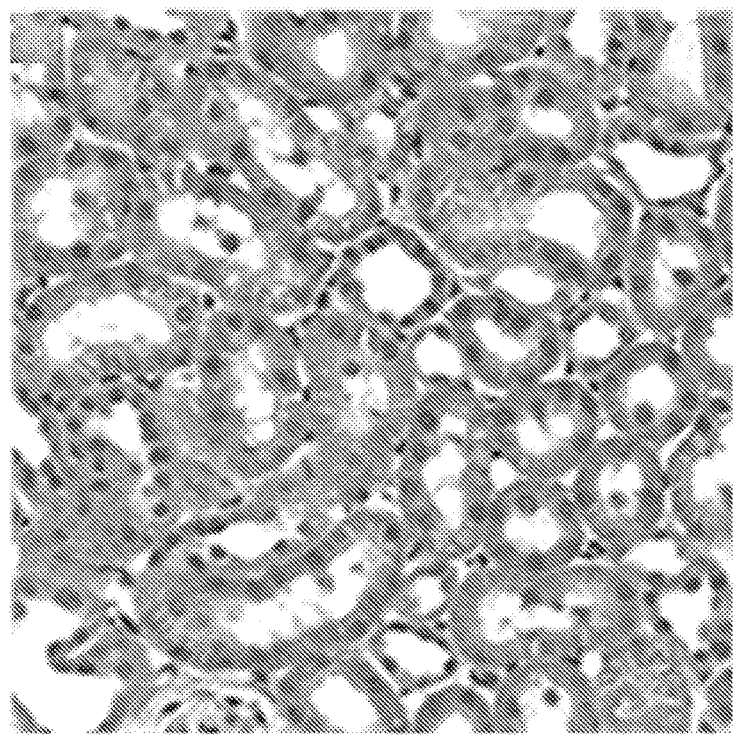
FIGS. 6A and 6B depict H&E stain of kidney syngenic graft samples obtained on POD 6 after transplantation. The graft tissue morphology and integrity is partially protected in the Intralipid®-treated graft kidney (FIG. 6A) compared to that of the graft kidney of the untreated group (FIG. 6B). Scale bar represents 40 μm.
Figure 6B:
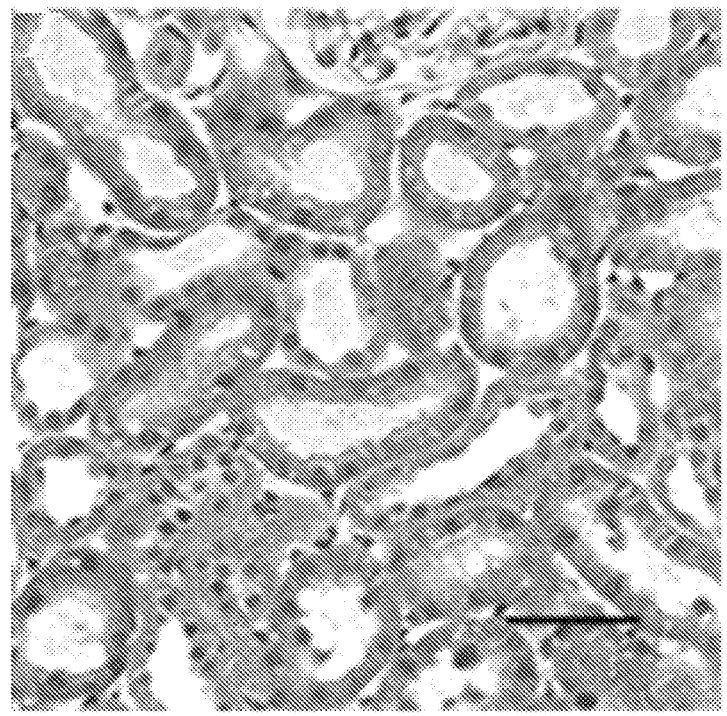

The results from both the acute kidney IRI model and the heart transplantation model indicate that Intralipid® can protect the grafts against IRI (See FIGS. 5 and 6). The grafts from both Intralipid® pre- and post-treatment groups were better protected, which was observed by both better graft function and reduced immune-cell infiltration, as revealed by MRI and pathology examinations.

In the heart allograft, the myocardium integrity was largely preserved in Intralipid®-treated groups (FIG. 5, top panel) compared to the untreated group (FIG. 5, bottom panel) as revealed by H&E staining (see FIGS. 5A, 5D). Both innate and adaptive immune responses were attenuated in Intralipid®-treated grafts as a markedly reduced number of ED1$^+$ cells (mainly monocytes/macrophages, FIGS. 5B, 5E) and CD3$^+$ cells (T-cells, FIGS. 5C, 5F) were seen in the treated-allograft tissue when compared with untreated groups. On POD 7, severe rejection occurred in allograft hearts of the untreated group, with abundant ED1$^+$ cells and CD3$^+$ cells infiltrating in the whole graft tissue, whereas there were significantly fewer infiltrates in the Intralipid®-treated heart graft (FIG. 5). These results are consistent with results showing allograft heart failure on POD 7 if no treatment is administered (see, Wu, et al., *Methods Enzymol.*, 386:73-105 (2004)). With the Intralipid® treatment, the grafts were protected from injury, showing marked improvement in myocardial integrity and less mononuclear cell infiltration on POD 7.

In the kidney model, H&E staining of kidney syngenic graft samples obtained on POD 6 after transplantation revealed that the morphology and integrity of the graft tissue was partially protected with the Intralipid® treatment (FIG. 6, Panel A) compared with the untreated group (FIG. 6, panel B). The interstitial and tubular edema appear more prominent in the graft of the control groups than in the grafts treated with Intralipid®.

Without being bound to a particular theory, the mechanism for Intralipid® protection against IRI can be through the modulation of cell-mediated pro-inflammatory responses, which promote acute organ damage and enhances allograft rejection (see, Tanaka, et al., *J. Heart Lung Transplant*, 24:1906-1914 (2005); Knight, et al., *J. Surg. Res.*, 113:201-207 (2003); and Kinsey, et al., *Kidney International*, 77:771-780 (2010)). The results from flow cytometry analysis revealed that Tregs contribute to the protective effect of Intralipid® against IRI and transplant rejection (FIG. 7). Compared with Tregs in the blood of untreated recipients (FIG. 7C), the percentage of Tregs out of total CD4$^+$ T-cells increased ~2.5 fold in the blood of Intralipid®-treated allograft recipients (FIG. 7D). These data implicate Intralipid® as an important immune modulator in transplantation. Although the IRI injury is a complex cascade, numerous mediators from the innate immune system seem to be key factors. The results described herein show that Intralipid® therapy at various time points prior to and/or after onset of IRI can effectively protect the heart and kidney against IRI and reduce allograft rejection. The data show that Intralipid® has beneficial effects on protecting the graft from IRI and can attenuate rejection due to its modulation of cell-mediated pro-inflammatory responses.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing organ transplant rejection due to ischemia or ischemic reperfusion injury in a human subject, the method comprising administering a fat emulsion, wherein the fat emulsion comprises 20% soybean oil, 1.2% Egg yolk phospholipid, and 2.25 glycerin, to the subject before the subject undergoes an organ transplant, wherein the fat emulsion is administered between 24 hours before and 24 hours after the organ transplantation.

2. The method of claim 1, wherein the fat emulsion is administered between 0.3 and 4 hours before the organ transplantation.

3. The method of claim 1, wherein the fat emulsion is administered between 0.3 and 3 hours before the organ transplantation.

4. The method of claim 1 wherein the fat emulsion is administered between 0.5 and 1.5 hours before the organ transplantation.

5. The method of claim 1, wherein the fat emulsion is administered between 4 and 10 hours before the organ transplantation.

6. The method of claim 1, wherein the fat emulsion is administered between 10 and 24 hours before the organ transplantation.

7. The method of claim 1, wherein the fat emulsion is administered between 10 and 15 hours before the organ transplantation.

8. The method of claim 1, wherein said fat emulsion is administered about 1 hour before the organ transplantation.

9. The method of claim 1, wherein the fat emulsion is administered intravenously to the subject.

10. The method of claim 1, wherein the organ transplant is a heart transplant.

11. The method of claim 1, wherein the organ transplant is a kidney transplant.

12. The method of claim 1, wherein the organ transplant is a liver transplant.

13. The method of claim 1, wherein the organ transplant is a lung transplant.

14. The method of claim 1, wherein the organ transplant is a pancreas transplant.

15. The method of claim 1, wherein the organ transplant rejection is due to ischemia.

16. The method of claim 1, wherein the organ transplant rejection is due to an ischemic reperfusion injury.

* * * * *